(12) United States Patent
Feng et al.

(10) Patent No.: US 9,672,639 B1
(45) Date of Patent: Jun. 6, 2017

(54) BIOLUMINESCENCE TOMOGRAPHY RECONSTRUCTION BASED ON MULTITASKING BAYESIAN COMPRESSED SENSING

(71) Applicant: Beijing University of Technology, Beijing (CN)

(72) Inventors: Jinchao Feng, Beijing (CN); Kebin Jia, Beijing (CN); Huijun Wei, Beijing (CN)

(73) Assignee: Beijing University of Technology, Beijing (CN)

( * ) Notice: Subject to any disclaimer, the term of this patent is extended or adjusted under 35 U.S.C. 154(b) by 0 days.

(21) Appl. No.: 15/108,394

(22) PCT Filed: Jul. 21, 2015

(86) PCT No.: PCT/CN2015/084555
§ 371 (c)(1),
(2) Date: Jun. 27, 2016

(87) PCT Pub. No.: WO2017/004851
PCT Pub. Date: Jan. 12, 2017

(30) Foreign Application Priority Data

Jul. 8, 2015 (CN) .......................... 2015 1 0397424

(51) Int. Cl.
*G06T 11/00* (2006.01)
*A61B 5/00* (2006.01)
*G06T 15/50* (2011.01)

(52) U.S. Cl.
CPC .......... *G06T 11/005* (2013.01); *A61B 5/0071* (2013.01); *A61B 5/0073* (2013.01); *A61B 5/7225* (2013.01); *A61B 5/7267* (2013.01); *G06T 15/506* (2013.01); *A61B 2503/40* (2013.01); *A61B 2576/00* (2013.01); *G06T 2210/41* (2013.01)

(58) Field of Classification Search
CPC .... G06T 11/003; G06T 11/005; G06T 11/006; G06T 15/506; G06T 2207/10072; G06T 2207/10101; A61B 5/0033; A61B 5/0071; A61B 5/0073
See application file for complete search history.

(56) References Cited

U.S. PATENT DOCUMENTS

| | | | |
|---|---|---|---|
| 8,094,149 B2 * | 1/2012 | Tian et al. | 345/419 |
| 2007/0244395 A1 | 10/2007 | Wang et al. | 600/476 |
| 2013/0108132 A1 * | 5/2013 | Klose | G06T 7/0012 382/131 |

FOREIGN PATENT DOCUMENTS

| | | |
|---|---|---|
| CN | 101342075 A | 1/2009 |
| CN | 103271723 A | 9/2013 |

* cited by examiner

*Primary Examiner* — Andrew W Johns
(74) *Attorney, Agent, or Firm* — Tian IP & Technology, LLC.

(57) ABSTRACT

Implementations of the present disclosure relate to methods for reconstruction for bioluminescence tomography based on a method of multitask Bayesian compressed sensing in the field of medical image processing. The method includes the following operations. Firstly the high order approximation model is used to model the law of light propagation in biological tissues, then the inner-correlation among multispectral measurements is researched based on multitask learning method and incorporated into a reconstruction algorithm of bioluminescence tomography as prior information to reduce ill-posedness of BLT reconstruction, and then on this basis, three-dimensional reconstruction of bioluminescent source is realized. Compared with other reconstruction algorithms for BLT, the correlation among multispectral measurements is incorporated into the disclosure and the ill-posedness of BLT reconstruction is reduced. The bioluminescent source can be reconstructed and located accurately using the proposed algorithm, and computational efficiency can be greatly improved.

1 Claim, 8 Drawing Sheets

Top arrow (b)
Middle arrow (c)
Bottom arrow (d)

BIOLUMINESCENCE TOMOGRAPHY RECONSTRUCTION BASED ON MULTITASKING BAYESIAN COMPRESSED SENSING

CROSS REFERENCE TO RELATED APPLICATION

This application is a national stage application of International application number PCT/CN2015/084555, filed Jul. 21, 2015, titled "Bioluminescence tomography reconstruction based on multitasking Bayesian compressed sensing," which claims the priority benefit of Chinese Patent Application No. 201510397424.0, filed on Jul. 8, 2015, which is hereby incorporated by reference in its entirety.

TECHNICAL FIELD

The disclosure belongs to the field of medical image processing, and more particularly to a reconstruction method for bioluminescence tomography based on a method of multitask Bayesian compressed sensing.

BACKGROUND

Optical molecular imaging is a rapidly developing technique of molecular imaging, which combines optical process with certain molecular properties. Optical molecular imaging analyzes and processes bioluminescence or excited fluorescence in objectives, and studies them qualitatively and quantitatively.

Representative imaging methods of optical molecular imaging technology are fluorescence imaging and bioluminescent imaging (BLI). Both of them belong to two-dimensional luminescent imaging technology. Although the technology is convenient and simple, it has limitations in application, especially for imaging depth, two-dimensional fluorescence image that may not reflect the information of light source depth and hard to quantify it. The two technologies mentioned above can only reflect projection information of fluorescent probes in organisms at a certain angle, which is generated by superposition of multiple depths signals. So, two-dimensional imaging technology has a very low resolution.

BLT developed based on two-dimensional bioluminescent imaging technology has become an important branch of optical molecular imaging because BLT can reflect the information of signal depth. Bioluminescence tomography technology works not by excitation of an external light source, but by a biochemical luminescence reaction in organisms. Photons generated in organisms propagate in a certain way in the biological tissue and constantly interact with it such as to reach body surface. Finally, distribution of the bioluminescent source in a small animal can be reconstructed using the bioluminescent images acquired on the surface of biological tissue by a high sensitivity detector, which reveals activity laws of molecules in vivo in essence.

The photons in biological tissue do not transmit along a straight line, but experience a lot of scattering process, which leads to BLT inverse problems: a highly ill-posed problem in mathematics. And small measurement disturbance from outside will bring great changes to reconstruction results. The researchers did a lot of work to reduce the ill-posedness usually by providing different prior knowledge to the problem from different angles.

The existing methods reducing ill-posedness are mostly based on multiplying spectral information and sparsity of light sources to study BLT reconstruction methods. However, the correlation among multi-spectra is not considered. In mathematics, the method of multi-spectra increases the known quantity of the equation to be solved, which can improve solving results. For BLT, in the method based on multi-spectra, the light source is reconstructed by the data obtained using multiple filters from different wavelengths, while the light source is remained unchanged. In fact, measurements among multi-spectra are not independent, but interrelated, and their common task is the reconstruction of the bioluminescent source. Therefore, the quality of reconstructed BLT images will be likely improved if the correlation among multi-spectra is considered into reconstruction. Based on this, a BLT reconstruction method based on inner-correlation of multi-spectra is proposed in the disclosure.

The disclosure is based on a multitask learning method. Firstly a high order approximation model is used to model the law of light transmission in the biological tissue, then inner-correlation among multi-spectra is researched based on the multitask learning method, and finally on this basis three-dimensional reconstruction of the bioluminescent source is realized.

SUMMARY

To solve the above problems existing in reconstruction algorithms for bioluminescence tomography, the disclosure proposes a method based on multitask learning. A high order approximation model is used to model the law of light propagation in the biological tissue, and inner-correlation among multi-spectra is researched based on multitask learning method, and finally on this basis three-dimensional reconstruction of a bioluminescent source is realized.

The technical scheme adopted in the disclosure is: firstly, a high order approximation model is used to model the law of light propagation in the biological tissue, and inner-correlation among multi-spectra is researched based on multitask learning method and incorporated into the reconstruction algorithm as prior information to reduce the ill-posedness of BLT reconstruction, finally on this basis three-dimensional reconstruction of the bioluminescent source is realized. Specifically, the following steps are provided as follow.

Step one, defining the problems and initialization—obtaining values of P spectral bands at M measurement points, and setting gamma prior distribution $\alpha_0$ with the shape parameter a and scale parameter b, wherein $\alpha_0^{-1}$ is the variance of emission light measurements $\Phi(\tau_i)$ with Gaussian distribution.

Two models can be adopted to simulate the law of light propagation in a biological tissue: radiative transfer equation and diffusion equation. Radiative transfer equation is a mathematical model describing accurately the law of light propagation, but the solution of RTE is very difficult even under a very simplified condition, and the amount of calculation is very large. Diffusion equation is the low-order approximation of the radiative transfer equation, and the solution of which is simple but the precision is low. Furthermore, the application of the diffusion equation must meet conditions of biological tissues with strong scattering and low absorption. It is not suitable for the condition that the light source is located on the boundaries of biological tissues, which limits the application of diffusion equation in the biomedical fields. Based on this, simplified spherical harmonics approximation ($SP_N$) equations are adopted in the disclosure. The model may describe accurately the light propagation in a biological tissue with strong scattering and low absorption, at the same time, it has a modest computational complexity. Instead of diffusion approximation transfer equation, the model is used to accurately simulate the law of the light propagation in the biological tissue to improve precision of forward solution.

Given the effect of spectrum, $SP_7$ model include four equations at band $\tau_i$ and position r:

$$-\nabla \cdot \frac{1}{3\mu_{a1}(r,\tau_i)}\nabla\varphi_1(r,\tau_i) + \mu_a(r,\tau_i)\varphi_1(r,\tau_i) = \tag{1}$$

$$S(r,\tau_i) + \left(\frac{2}{3}\mu_a(r,\tau_i)\right)\varphi_2(r,\tau_i) -$$

$$\left(\frac{8}{15}\mu_a(r,\tau_i)\right)\varphi_3(r,\tau_i) + \left(\frac{16}{35}\mu_a(r,\tau_i)\right)\varphi_4(r,\tau_i)$$

$$-\nabla \cdot \frac{1}{7\mu_{a3}(r,\tau_i)}\nabla\varphi_2(r,\tau_i) + \left(\frac{4}{9}\mu_a(r,\tau_i) + \frac{5}{9}\mu_{a2}(r,\tau_i)\right)\varphi_2(r,\tau_i) = \tag{2}$$

$$-\frac{2}{3}S(r,\tau_i) + \left(\frac{2}{3}\mu_a(r,\tau_i)\right)\varphi_1(r,\tau_i) +$$

$$\left(\frac{16}{45}\mu_a(r,\tau_i) + \frac{4}{9}\mu_{a2}(r,\tau_i)\right)\varphi_3(r,\tau_i) -$$

$$\left(\frac{32}{105}\mu_a(r,\tau_i) + \frac{8}{21}\mu_{a2}(r,\tau_i)\right)\varphi_4(r,\tau_i)$$

$$-\nabla \cdot \frac{1}{11\mu_{a5}(r,\tau_i)}\nabla\varphi_3(r,\tau_i) + \tag{3}$$

$$\left(\frac{64}{225}\mu_a(r,\tau_i) + \frac{16}{45}\mu_{a2}(r,\tau_i) + \frac{9}{25}\mu_{a4}(r,\tau_i)\right)\varphi_3(r,\tau_i) =$$

$$\frac{8}{15}S(r,\tau_i) - \left(\frac{8}{15}\mu_a(r,\tau_i)\right)\varphi_1(r,\tau_i) +$$

$$\left(\frac{16}{45}\mu_a(r,\tau_i) + \frac{4}{9}\mu_{a2}(r,\tau_i)\right)\varphi_2(r,\tau_i) +$$

$$\left(\frac{128}{525}\mu_a(r,\tau_i) + \frac{32}{105}\mu_{a2}(r,\tau_i) + \frac{54}{175}\mu_{a4}(r,\tau_i)\right)\varphi_4(r,\tau_i)$$

$$-\nabla \cdot \frac{1}{15\mu_{a7}(r,\tau_i)}\nabla\varphi_4(r,\tau_i) + \tag{4}$$

$$\left(\frac{256}{225}\mu_a(r,\tau_i) + \frac{64}{245}\mu_{a2}(r,\tau_i) + \frac{324}{1225}\mu_{a4}(r,\tau_i) + \frac{13}{49}\mu_{a6}(r,\tau_i)\right)$$

$$\varphi_4(r,\tau_i) = -\frac{16}{35}S(r,\tau_i) + \left(\frac{16}{35}\mu_a(r,\tau_i)\right)\varphi_1(r,\tau_i) -$$

$$\left(\frac{32}{105}\mu_a(r,\tau_i) + \frac{8}{21}\mu_{a2}(r,\tau_i)\right)\varphi_2(r,\tau_i) +$$

$$\left(\frac{128}{525}\mu_a(r,\tau_i) + \frac{32}{105}\mu_{a2}(r,\tau_i) + \frac{54}{175}\mu_{a4}(r,\tau_i)\right)\varphi_3(r,\tau_i)$$

Wherein S represents light function; $\mu_a$ is light absorption coefficient; $\mu_s$ is light scattering coefficient; $\mu_{ai}=\mu_a+\mu_s(1-g^i)$, $g^i$ is anisotropic factor; $\phi_i$ represents the linear combination of Legendre moments $\phi_i$ of radiosity and can be represented as:

$$\begin{cases} \varphi_1 = \phi_0 + 2\phi_2 \\ \varphi_2 = 3\phi_2 + 4\phi_4 \\ \varphi_3 = 5\phi_4 + 6\phi_6 \\ \varphi_4 = 7\phi_6 \end{cases}$$

Based on the $SP_7$ equation, set $\phi_6=\phi_4=0$, and remain formula (1) and (2), and $SP_3$ equations are obtained:

$$-\nabla \cdot \frac{1}{3\mu_{a1}(r,\tau_i)}\nabla\varphi_1(r,\tau_i) + \tag{6}$$

$$\mu_a(r,\tau_i)\varphi_1(r,\tau_i) - \frac{2}{3}\mu_a(r,\tau_i)\varphi_2(r,\tau_i) = S(r,\tau_i)$$

$$-\left(\frac{2}{3}\mu_a(r,\tau_i)\right)\varphi_1(r,\tau_i) - \nabla \cdot \frac{1}{7\mu_{a3}(r,\tau_i)}\nabla\varphi_2(r,\tau_i) + \tag{7}$$

$$\left(\frac{4}{9}\mu_a(r,\tau_i) + \frac{5}{9}\mu_{a2}(r,\tau_i)\right)\varphi_2(r,\tau_i) = -\frac{2}{3}S(r,\tau_i)$$

Based on the boundary conditions of $SP_7$, set $\phi_6=\phi_4=0$, and the boundary conditions of $SP_3$ are obtained:

$$\left(\frac{1}{2} + A_1\right)\varphi_1(r,\tau_i) + \left(\frac{1+B_1}{3\mu_{a1}(r,\tau_i)}\right)\vec{n}(r,\tau_i) \cdot \nabla\varphi_1(r,\tau_i) = \tag{8}$$

$$\left(\frac{1}{8} + C_1\right)\varphi_2(r,\tau_i) + \left(\frac{D_1}{\mu_{a3}(r,\tau_i)}\right)\vec{n}(r,\tau_i) \cdot \nabla\varphi_2(r,\tau_i)$$

$$\left(\frac{7}{24} + A_2\right)\varphi_2(r,\tau_i) + \left(\frac{1+B_2}{7\mu_{a3}(r,\tau_i)}\right)\vec{n}(r,\tau_i) \cdot \nabla\varphi_2(r,\tau_i) = \tag{9}$$

$$\left(\frac{1}{8} + C_2\right)\varphi_1(r,\tau_i) + \left(\frac{D_2}{\mu_{a1}(r,\tau_i)}\right)\vec{n}(r,\tau_i) \cdot \nabla\varphi_1(r,\tau_i)$$

Wherein $\vec{n}$ represents the outward unit normal vector perpendicular to the boundary; $A_i$, $B_i$ and $C_i$ are a series of constants which are related to the angle distance of boundary reflectivity. The corresponding surface emission light $\Phi(r,\tau_i)$ is:

$$\Phi(r,\tau_i) = \left(\frac{1}{4} + J_0\right)\varphi_1(r,\tau_i) - \left(\frac{0.5 + J_1}{3\mu_{a1}\varphi_1(r,\tau_i)}\right)\vec{n} \cdot \nabla\varphi_1(r,\tau_i) -$$

$$\left(\frac{1}{16} + \frac{2J_0 - J_2}{3}\right)\varphi_2(r,\tau_i) - \left(\frac{J_3}{7\mu_{a1}\varphi_2(r,\tau_i)}\right)\vec{n} \cdot \nabla\varphi_2(r,\tau_i)$$

Wherein $J_0, \ldots, J_3$ are a series of constants.

Step two, constructing the linear relationship—based on finite element method to discretize $SP_3$ diffusion equation, and constructing the linear model between boundary measurements and unknown light source for each wavelength;

In the formula (6) and (7), $S(r, \tau_i)$ represents the distribution of bioluminescent source and also the unknown quantity to be solved. In order to solve the $SP_3$ equation and its boundary conditions using finite element method, firstly two $SP_3$ equations should be written in corresponding weak solution forms:

$$\int_\Omega \left(-\nabla \cdot \frac{1}{3\mu_{a1}(r,\tau_i)}\nabla\varphi_1(r,\tau_i) + \mu_a(r,\tau_i)\varphi_1(r,\tau_i) - \frac{2}{3}\mu_a(r,\tau_i)\varphi_2(r,\tau_i)\right)$$

$$\Psi(r,\tau_i)dr = \int_\Omega S(r,\tau_i)\Psi(r,\tau_i)dr$$

$$\int_\Omega \left(-\left(\frac{2}{3}\mu_a(r,\tau_i)\right)\varphi_1(r,\tau_i) - \nabla \cdot \frac{1}{7\mu_{a3}(r,\tau_i)}\nabla\varphi_2(r,\tau_i) + \right.$$

$$\left.\left(\frac{4}{9}\mu_a(r,\tau_i) + \frac{5}{9}\mu_{a2}(r,\tau_i)\right)\varphi_2(r,\tau_i)\right)$$

$$\Psi(r,\tau_i)dr = \int_\Omega \left(-\frac{2}{3}S(r,\tau_i)\right)\Psi(r,\tau_i)dr$$

Wherein, $\Psi(r, \tau_i)$ is test function, and two boundary conditions for formula (8) and (9) also should be written in corresponding weak solution forms:

$$\int_\Omega \left(\left(\frac{1}{2}+A_1\right)\varphi_1(r,\tau_i)+\left(\frac{1+B_1}{3\mu_{a1}(r,\tau_i)}\right)\vec{n}(r,\tau_i)\cdot\nabla\varphi_1(r,\tau_i)\right)\Psi(r,\tau_i)dr =$$

$$\int_\Omega \left(\left(\frac{1}{8}+C_1\right)\varphi_2(r,\tau_i)+\left(\frac{D_1}{\mu_{a3}(r,\tau_i)}\right)\vec{n}(r,\tau_i)\cdot\nabla\varphi_2(r,\tau_i)\right)\Psi(r,\tau_i)dr$$

$$\int_\Omega \left(\left(\frac{7}{24}+A_2\right)\varphi_2(r,\tau_i)+\left(\frac{1+B_2}{7\mu_{a3}(r,\tau_i)}\right)\vec{n}(r,\tau_i)\cdot\nabla\varphi_2(r,\tau_i)\right)\Psi(r,\tau_i)dr =$$

$$\int_\Omega \left(\left(\frac{1}{8}+C_2\right)\varphi_1(r,\tau_i)+\left(\frac{D_2}{\mu_{a1}(r,\tau_i)}\right)\vec{n}(r,\tau_i)\cdot\nabla\varphi_1(r,\tau_i)\right)\Psi(r,\tau_i)dr$$

Then the weak solution forms of the boundary conditions are incorporated into that for the SP$_3$ equation using Green's formula.

$$\int_\Omega \left(\frac{1}{3\mu_{a1}}\nabla\varphi_1(r,\tau_i)+\mu_a\varphi_1(r,\tau_i)\psi(r,\tau_i)-\frac{2}{3}\mu_a\varphi_2(r,\tau_i)\psi(r,\tau_i)\right)dr -$$

$$\int_{\partial\Omega}\left(\frac{e_1}{3\mu_{a1}}\nabla\varphi_1(r,\tau_i)+\frac{e_2}{3\mu_{a1}}\varphi_2(r,\tau_i)\right)\psi(r,\tau_i)dr = \int_\Omega S(r,\tau_i)\psi(r,\tau_i)dr$$

$$\int_\Omega \left(\frac{1}{7\mu_{a3}(r,\tau_i)}\nabla\varphi_2(r,\tau_i)\cdot\nabla\psi(r,\tau_i)+\right.$$

$$\left(\frac{4}{9}\mu_a(r,\tau_i)+\frac{5}{9}\mu_{a2}(r,\tau_i)\right)\varphi_2(r,\tau_i)\psi(r,\tau_i)-$$

$$\left.\left(\frac{2}{3}\mu_a(r,\tau_i)\right)\varphi_1(r,\tau_i)\psi(r,\tau_i)\right)dr = \int_\Omega \left(-\frac{2}{3}S(r,\tau_i)\right)\psi(r,\tau_i)dr$$

Wherein $e_1$, $e_2$, $e_3$ and $e_4$ are respectively:

$$e_1 = \frac{1}{W}\left(\frac{D_1(1+8C_2)}{8\mu_{a3}}-\frac{(1+B_2)(1+2A_1)}{14\mu_{a3}}\right)$$

$$e_2 = \frac{1}{W}\left(\frac{(1+B_2)(1+8C_2)}{56\mu_{a3}}-\frac{D_1(7+24A_2)}{24\mu_{a3}}\right)$$

$$e_3 = \frac{1}{W}\left(\frac{(1+B_1)(1+8C_2)}{24\mu_{a1}}-\frac{D_2(2+A_1)}{2\mu_{a1}}\right)$$

$$e_4 = \frac{1}{W}\left(\frac{D_2(1+8C_1)}{8\mu_{a1}}-\frac{(1+B_1)(7+24A_2)}{72\mu_{a1}}\right)$$

In the above formulas, the form for W is as follow:

$$W = \frac{(1+B_1)(1+B_2)}{21\mu_{a1}\mu_{a3}}-\frac{D_1D_2}{\mu_{a1}\mu_{a3}}$$

For mesh generation, the distribution of light source $S(r,\tau_i)$ is written as $S(\tau_i)$ only related to the spectral band, when the corresponding basis function is selected, the whole stiffness matrix $M_{ij}$ is assembled, the SP$_3$ equations are discretized into the matrix equation as follow:

$$\begin{bmatrix} M_{11} & M_{12} \\ M_{21} & M_{22} \end{bmatrix}\begin{bmatrix}\varphi_1\\\varphi_2\end{bmatrix} = \begin{bmatrix} B & 0 \\ 0 & B \end{bmatrix}\begin{bmatrix} S(\tau_i) \\ -\frac{2}{3}S(\tau_i) \end{bmatrix}$$

Wherein B is the matrix of size N×N, $\phi_1$ and $\phi_1$ are two partitioned submatrices and can be represented as:

$\phi_1 = \frac{1}{3}B[3M_{12}^{-1}+2M_{22}^{-1}IM_{11}^{-1}M_{12}+2M_{21}^{-1}M_{22}^{-1}]S(\tau_i)$ $\phi_2 = \frac{1}{3}B[3M_{11}^{-1}+2M_{21}^{-1}IM_{11}^{-1}M_{12}+2M_{21}^{-1}M_{22}^{-1}]S(\tau_i)$ The linear relationship between the surface emission light $\Phi(\tau_i)$ and the distribution of unknown bioluminescent source $S(\tau_i)$ should be constructed. In the experiment, only the optical signals on the surface of organisms can be collected, so only the node values on the boundary of $\Phi(\tau_i)$ is remained and the rows which do not contain the nodes on the boundary of matrix are removed, and the equation is obtained as follow:

$\Phi(\tau_i)=\beta_1\phi_1+\beta_2\phi_2=\frac{1}{3}B(\beta_1[3M_{12}^{-1}+2M_{22}^{-1}IM_{11}^{-1}M_{12}+2M_{21}^{-1}M_{22}^{-1}]+\beta_2[3M_{11}^{-1}+2M_{21}^{-1}IM_{11}^{-1}M_{12}+2M_{21}^{-1}M_{22}^{-1}])S(\tau_i)=A(\tau_i)S(\tau_i)$ The above equation constructs the relationship between the distribution of unknown bioluminescent source and the boundary emission light, i.e.:

$\Phi(\tau_i)=A(\tau_i)S(\tau_i)$

In multispectral conditions, the energy ratio $\omega(\tau_i)$ of spectral bands is measured by spectrum analysis in advance, set S represent the total energy of all spectral bands of light sources, i.e. $S=\Sigma_{i=1}^P \omega(\tau_i)S(\tau_i)$, and p represent the number of spectral bands. All spectral bands of light sources and boundary measurements are incorporated, and the relationship between the distribution of unknown bioluminescent source and the boundary emission light in multispectral conditions is as follow:

$A_{mul}S=\Phi_{mul}$

Now, $$A_{mul} = \begin{bmatrix} \omega(\tau_1)A(\tau_1) \\ \omega(\tau_2)A(\tau_2) \\ \vdots \\ \omega(\tau_P)A(\tau_P) \end{bmatrix}, \Phi_{mul} = \begin{bmatrix} \Phi(\tau_1) \\ \Phi(\tau_2) \\ \vdots \\ \Phi(\tau_P) \end{bmatrix}$$

Step three, estimating the shared prior—based on empirical Bayesian maximum likelihood function, inferring parameter α which represents the correlation among multiwavelength;

In practical problems, the emission light measurement $\Phi(\tau_i)$ usually contains noise, if the noise obeys Gaussian random distribution with mean zero and variance $\alpha_0^{-1}$, the maximum likelihood function of $\Phi(\tau_i)$ related to the distribution of bioluminescent source $S(\tau_i)$ and $\alpha_0$ is represented as:

$$p(\Phi(\tau_i)\mid S(\tau_i),\alpha_0) = \left(\frac{\alpha_0}{2\pi}\right)^{\frac{M}{2}}\exp\left\{-\frac{\alpha_0}{2}\|\Phi(\tau_i)-A(\tau_i)S(\tau_i)\|_2^2\right\}$$

In order to describe the correlation among spectral bands, a multitask idea is introduced, and the whole light source is regarded as a whole task T, wherein $S(\tau_i)$ is the ith task model in T, and $S_j(\tau_i)$ represents the jth element of $S(\tau_i)$. If $S(\tau_i)$ obeys the Gaussian prior distribution with mean zero and parameter $\alpha_0$ obeys Gamma prior distribution, then:

$p(S(\tau_i)\mid\alpha,\alpha_0)=\Pi_{j=1}^N N(S_j(\tau_i)\mid 0,\alpha_0^{-1}\alpha_j^{-1})$ $p(\alpha_0\mid a,b)=Ga(\alpha_0\mid a,b)$ Wherein $\alpha=(\alpha_1,\ldots\alpha_j,\ldots\alpha_N)^T$ is hyper-parameter, representing prior information. Then, the values of $\alpha_j$ are identical in all spectral bands, i.e. α representing the correlation among various spectral bands, the empirical Bayesian method estimate the hyper-parameter α is used by maximizing the marginal likelihood function, then:

$$L = \sum_{i=1}^{p} \log p(\Phi(\tau_i) \mid \alpha) =$$

$$\sum_{i=1}^{p} \log \left( \int P(\Phi(\tau_i) \mid S(\tau_i), \alpha_0) P(S(\tau_i) \mid \alpha, \alpha_0) P(\alpha_0 \mid a, b) \right) dS_{\tau_i} d\alpha_0 =$$

$$-\frac{1}{2} \sum_{i=1}^{p} \left[ (n_i + 2a) \log(\Phi(\tau_i)^T B_i^{-1} \Phi(\tau_i) + b) + \frac{\log|B_i|}{2} \right] + const$$

Wherein, $B_i = I + A(\tau_i) \Lambda^{-1} A(\tau_i)^T, \Lambda^{-1} = \text{diag}(\alpha_1, \alpha_1, \ldots, \alpha_N).$ Step four, reconstructing unknown light source—based on the estimated $\hat{\alpha}$ of the known hyper-parameter and boundary measurements $\Phi_{mul}$, the bioluminescent source is reconstructed using maximum likelihood function.

After obtaining the estimated $\hat{\alpha}$, all spectral bands of light sources and boundary measurements are incorporated, and the maximum likelihood function of the unknown light source S can be represented as:

$$P(S \mid \Phi_{mul}, \hat{\alpha}) = \int P(S \mid \Phi_{mul}, \hat{\alpha}, \alpha_0) P(\alpha_0 \mid a, b) d\alpha_0 =$$

$$\frac{\Gamma\left(a + \frac{N}{2}\right) \left[ 1 + \frac{1}{2b} (S - \mu_{mul})^T \sum_{mul}^{-1} (S - \mu_{mul}) \right]^{-\left(a + \frac{N}{2}\right)}}{\Gamma(a)(2\pi b)^{N/2} |\sum_{mul}|^{1/2}}$$

Figure 1:
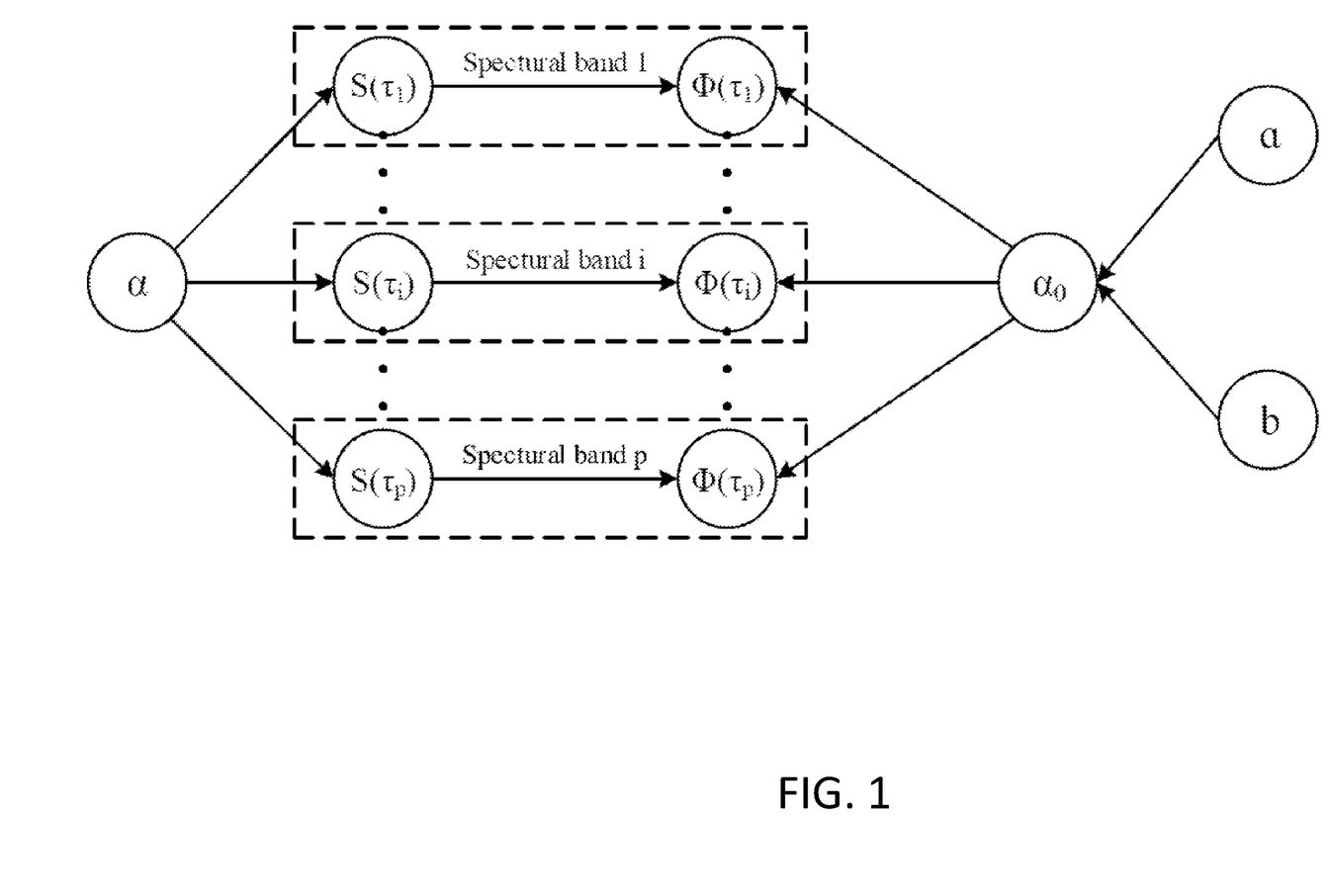
FIG. 1 shows a framework of a multitask model.

Wherein, $\mu_{mul} = \Sigma_{mul} A_{mul}^T \Phi_{mul}$ $\Sigma_{mul} = (A_{mul}^T A_{mul} - \Xi)^{-1}$ In the formula, $\Xi = \text{diag}(\hat{\alpha}_1, \hat{\alpha}_1, \ldots, \hat{\alpha}_N)$, the framework of multitask model is shown in FIG. 1.

The disclosure is based on multitask learning method. Firstly a high order approximation model is used to model the law of light propagation in the biological tissue, then inner-correlation among multi-spectra is researched based on multitask learning method, and finally on this basis three-dimensional reconstruction of the fluorescent source is realized. The reconstruction results show not only bioluminescent sources in a mouse body are accurately reconstructed and located in the disclosure, but computational efficiency has been greatly improved.

DETAILED DESCRIPTION OF THE PREFERRED EMBODIMENTS

The disclosure will be described in more detailed below accompanying drawings with preferred embodiments.

Figure 2:
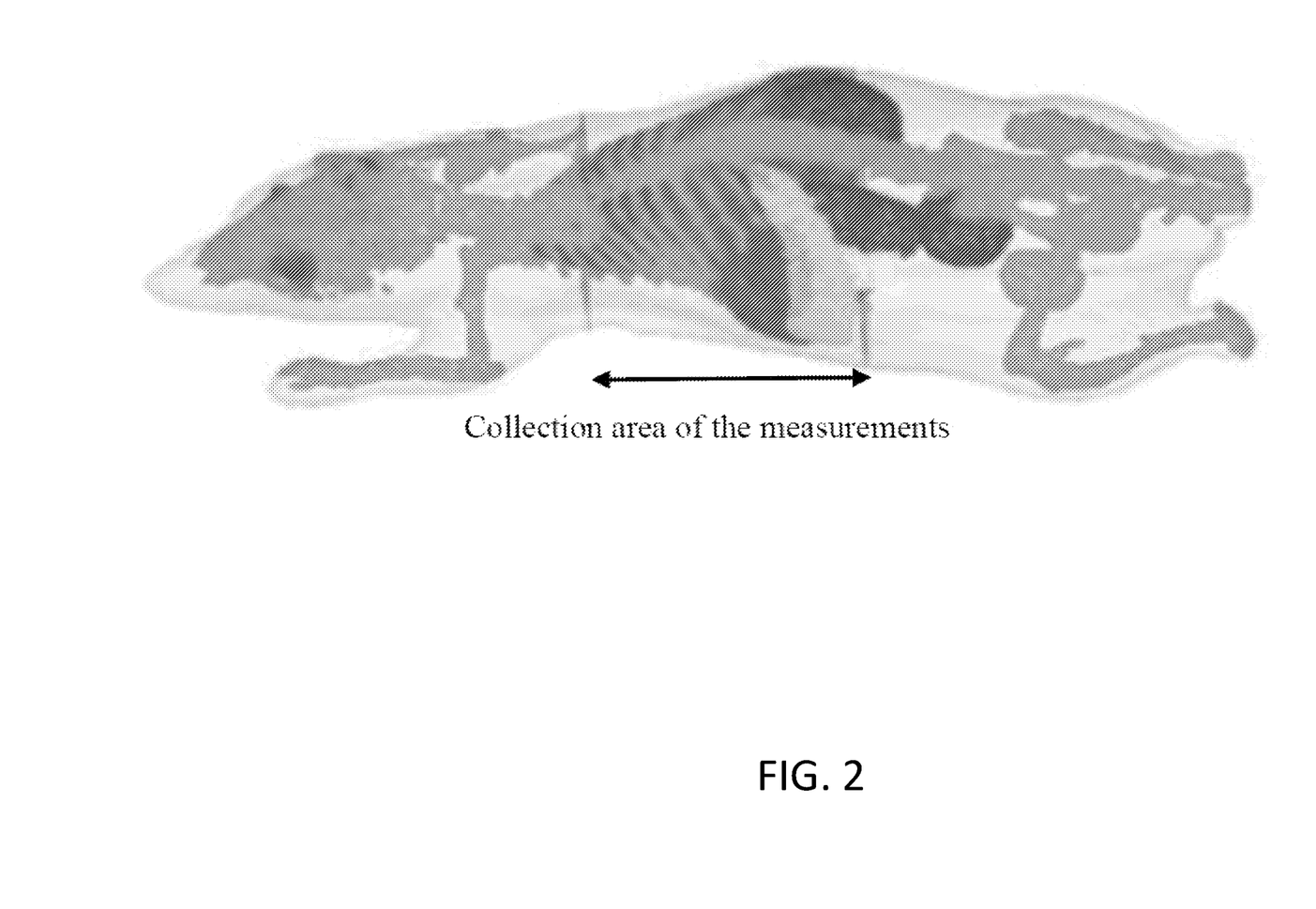
FIG. 2 shows a collection area of measurements of a digital mouse chest.

In order to test effectiveness of the proposed method in the disclosure, two simulation experiments were performed using heterogeneous digital mouse phantoms. In the experiments, parameters of optical properties of biological tissues were supposed to be known, and the detailed parameters were shown in table 1. The forward boundary measurements were obtained using finite element method in this disclosure. In order to avoid "inverse crime" effectively, forward data was obtained using $SP_3$ equation, a mesh of which contain 42342 nodes and 208966 tetrahedral units, and the mesh used in reconstruction contain 20196 nodes and 108086 tetrahedral units. Given the spectral distribution, two spectral bands adopted in the experiment are 620 nm and 700 nm, respectively. In order to simulate a collection of bioluminescent data, only the measurements of digital mouse chest (a total of 1311 boundary measurement points) were adopted, as shown in FIG. 2.

TABLE 1

Parameters of Optical Properties of Biological Tissues

| Biological Tissue | Spectral Band | Light Absorption Coefficient$^{\mu a}$ (mm$^{-1}$) | Light Absorption Coefficient$^{\mu s}$ (mm$^{-1}$) |
|---|---|---|---|
| Muscle | 620 nm | 0.086 | 0.429 |
|  | 700 nm | 0.0027 | 0.3792 |
| Liver | 620 nm | 0.345 | 0.678 |
|  | 700 nm | 0.23 | 0.648 |
| Lung | 620 nm | 0.195 | 2.173 |
|  | 700 nm | 0.13 | 2.124 |
| Bone | 620 nm | 0.06 | 2.495 |
|  | 700 nm | 0.039 | 2.34 |
| Heart | 620 nm | 0.058 | 0.963 |
|  | 700 nm | 0.038 | 0.905 |

Experiment 1

First group: in the first group experiment, a spherical light source with the radius of 1.5 mm was placed in a mouse lung, and the central position of which was (14.5, 44.0, 12.8) mm and the distance from the organism surface was 4.8 mm.

Figure 3:
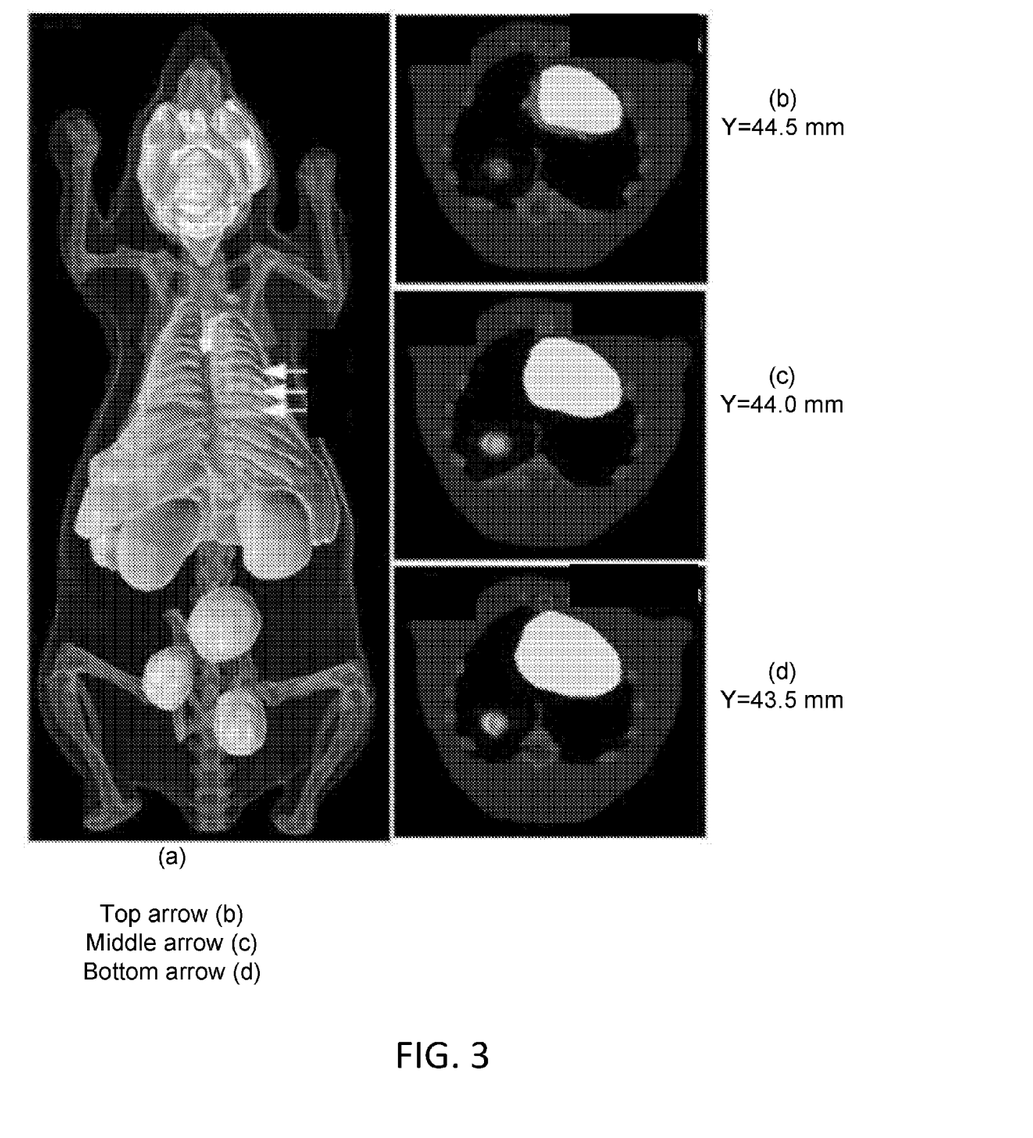
FIG. 3 shows reconstruction results of light sources in a lung (a) shows the reconstruction positions of the light sources in the lung, (b)-(d) show coronal slices of reconstructed results using BLT corresponding XCT. In (b)-(d), positions of real light sources marked by circles.

The bioluminescent source was reconstructed using the reconstruction algorithm proposed in the disclosure, and the reconstruction results were analyzed and shown in FIG. 3. It can be seen that the bioluminescent source can be reconstructed accurately using the method proposed in the disclosure, the central position of which was (14.69, 44.17, 14.69) mm and the absolute distance from the real light source was 0.28 mm.

Figure 4:
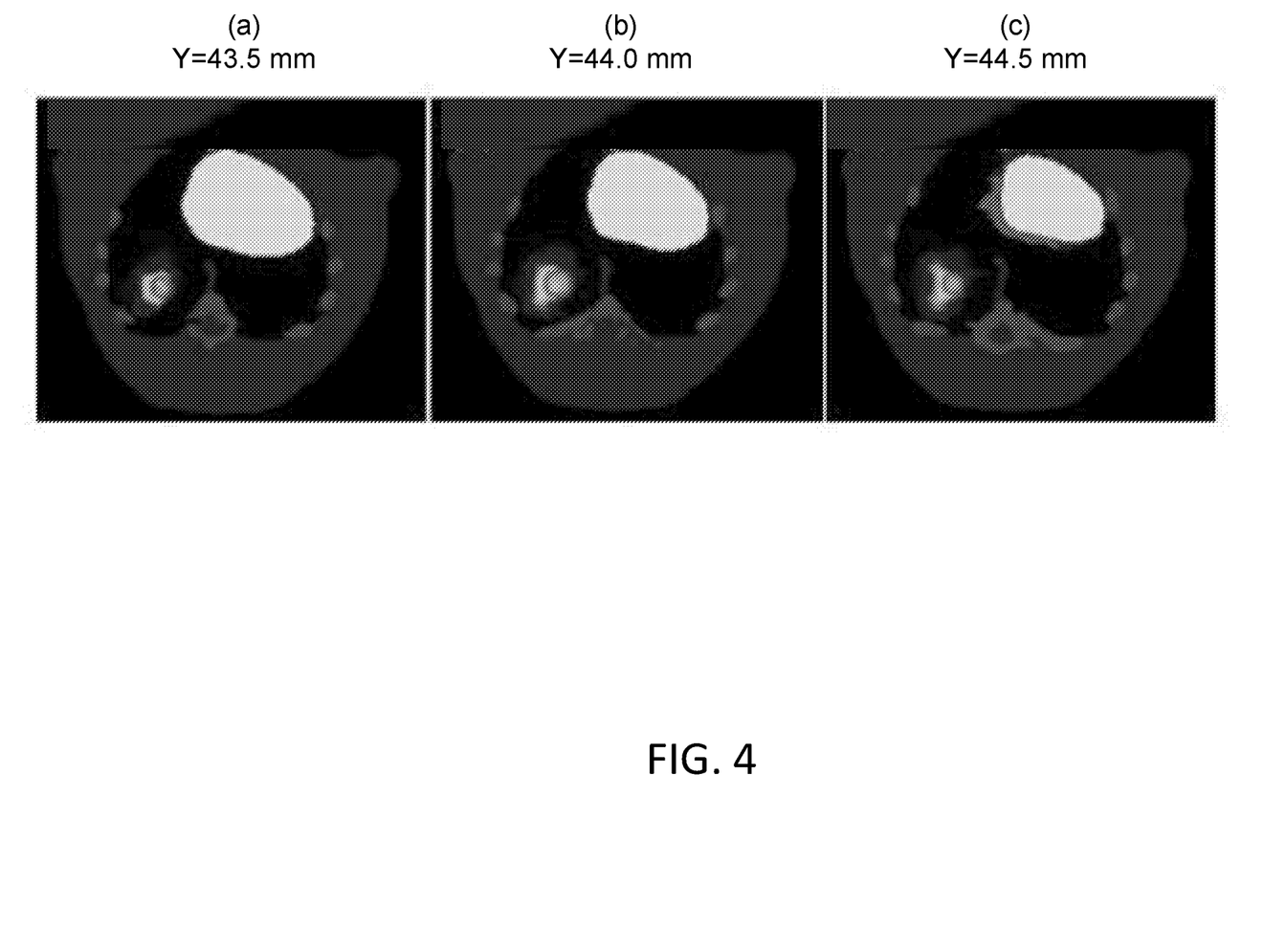
FIG. 4 shows reconstruction results of light sources based on L1 regularization reconstruction method (a)-(c) show coronal slices of reconstructed results using BLT corresponding to XCT, positions of the real light sources marked by circles.

Further, in order to verify its effectiveness, the algorithm proposed in the disclosure was compared with the reconstruction algorithm based on L1 regularization method, and the reconstruction results from the latter were shown in FIG. 4. The center position of the light source reconstructed based on L1 regularization method was (14.59, 43.63, 14.59) mm, and the distance from the real light source was 0.39 mm.

In addition, the computation time spent on reconstruction is 1773.9 seconds using L1 regularization method, whereas only 0.67 seconds spent on reconstruction using the algorithm proposed in this disclosure.

Second group: in the second group experiment, the light source with same size was placed in the liver, the central position of which was (22.0, 51.0, 22.0) mm, and the distance from the organism surface was 7.06 mm.

Figure 5:
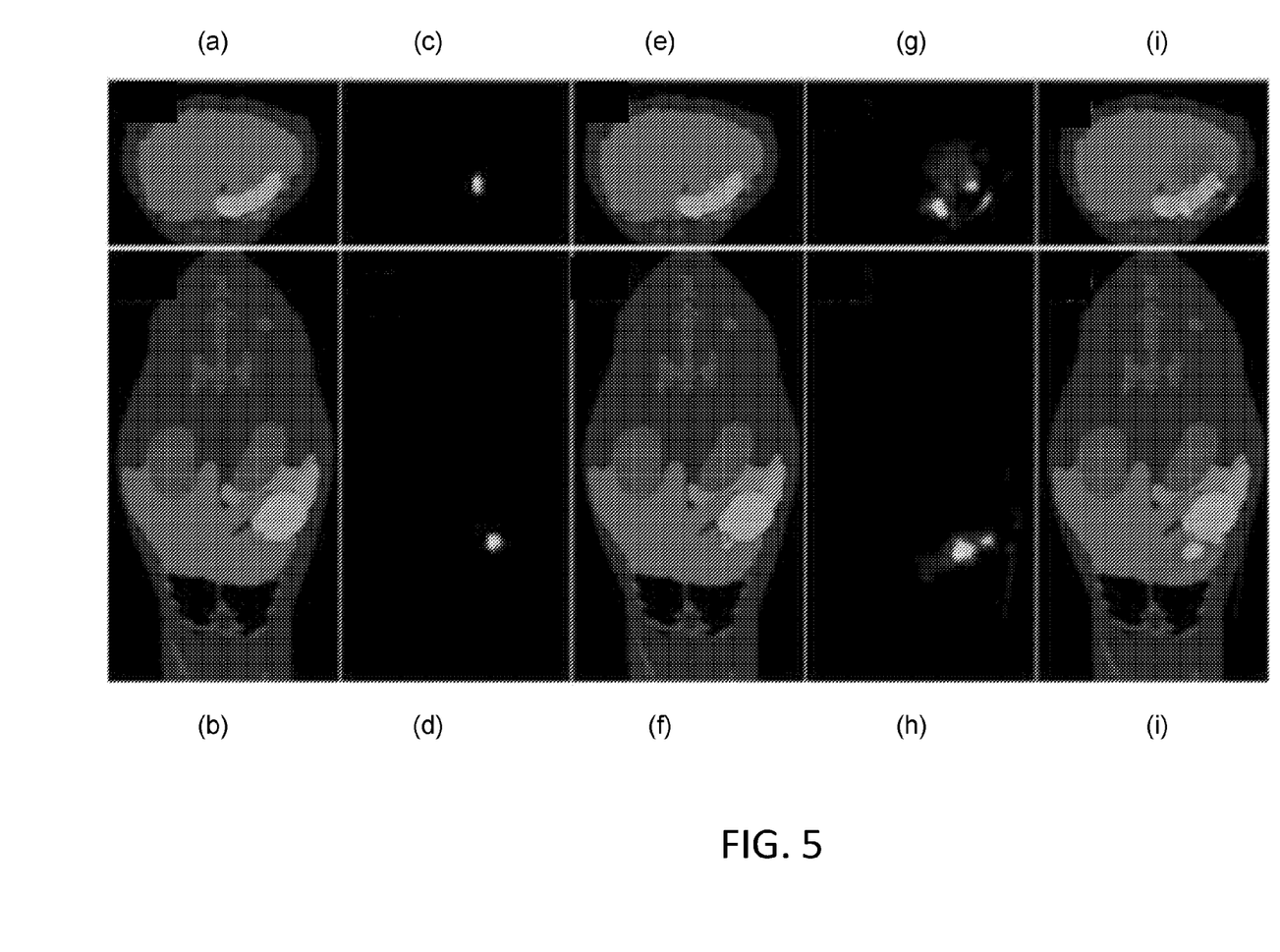
FIG. 5 shows reconstruction results of the light sources in a liver (a) and (b) show reconstructed slices using micro-CT. (c)-(f) show the distribution of light sources reconstructed based on the algorithm proposed in this disclosure, (g)-(j) show the reconstruction results using L1 norm regularization method. (c) and (i) show the coronal slices when y=51 mm, (f) and (j) show the cross section when z=12.97 mm. The positions of the real light sources are marked by circles.

Then, the light source was reconstructed using the algorithm proposed in the disclosure, and the results were shown in FIG. 5. It can be seen that the bioluminescent source can be reconstructed accurately using the algorithm proposed in the disclosure, the central position of which was (22.37, 50.68, 22.37) mm, and the absolute distance from the real light source was 0.5612 mm.

Figure 6:
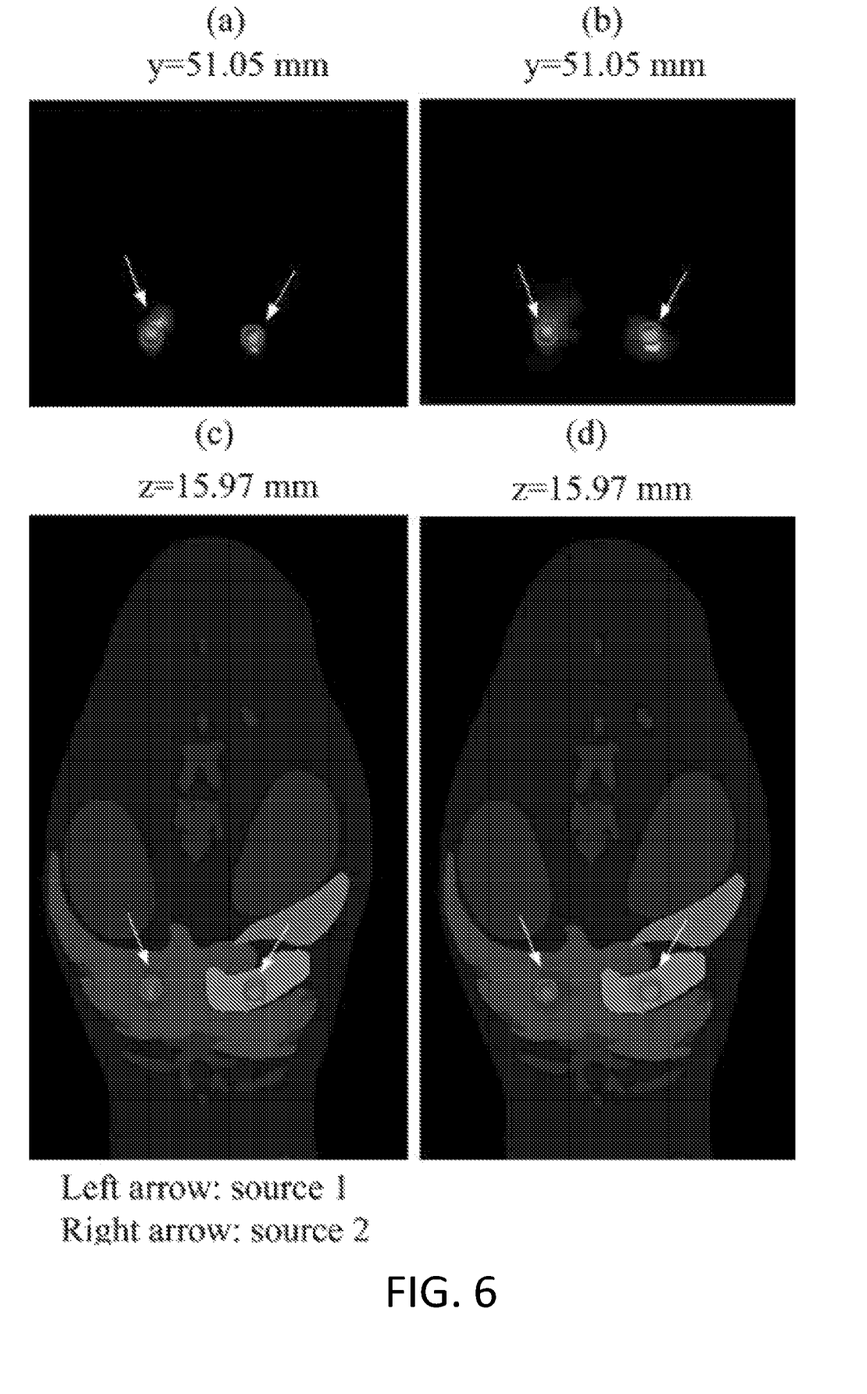
FIG. 6 shows reconstruction results based on two algorithms. (a) and (c) show the reconstruction results using the algorithm proposed in the disclosure, (b) and (d) show the reconstruction results using L1 norm regularization method. (a) and (b) show the coronal section when y=51.05 mm, (c) and (d) show the cross section when z=15.97. Positions of real light sources are marked by circles.

In order to verify the effectiveness of the algorithm, it was compared with the reconstruction algorithm based on L1 regularization method, and the reconstruction results of the latter were shown in FIG. 6. The center position of the light source reconstructed based on L1 regularization reconstruction method was (23.01, 50.06, 14.87) mm, and the distance from the real light source was 2.3239 mm.

Accordingly, it can be seen that the reconstruction based on L1 regularization method had poor effect and big errors when the reconstructed bioluminescent source was located at a deeper position of the biological tissue; whereas the fluorescent source can be located accurately using the method proposed in this disclosure. At the same time, the computation time of reconstruction was 1738.8 seconds using L1 regularization method, whereas only 0.936 seconds using the algorithm in this disclosure.

The summarizing quantitative comparison of the above two group experiments were performed, the reconstruction algorithm based on multitask compression sensing proposed in this disclosure was abbreviated to IRIRM, and the reconstruction algorithm based on L1 norm regularization was abbreviated to L1-RMRM. The comparison results were shown in table 2.

TABLE 2

The Summarizing Quantitative Comparison Between Two Algorithms

| Reconstruction Algorithm | Real Positions of the Light Sources | Reconstructed Positions | Position Error (mm) | Reconstruction Time(s) |
|---|---|---|---|---|
| IRIRM | (14.5, 44.0, 12.8) | (14.69, 44.17, 12.9) | 0.28 | 0.67 |
|  | (22.0, 51.0, 13.0) | (22.37, 50.68, 13.15) | 0.5612 | 0.936 |
| L1-RMRM | (14.5, 44.0, 12.8) | (14.59, 43.63, 12.88) | 0.39 | 1773.9 |
|  | (22.0, 51.0, 13.0) | (23.01, 50.06, 14.87) | 2.3239 | 1738.8 |

Experiment 2

In order to further test the effectiveness of the algorithm, the second experiment of double light sources was performed.

Figure 7:
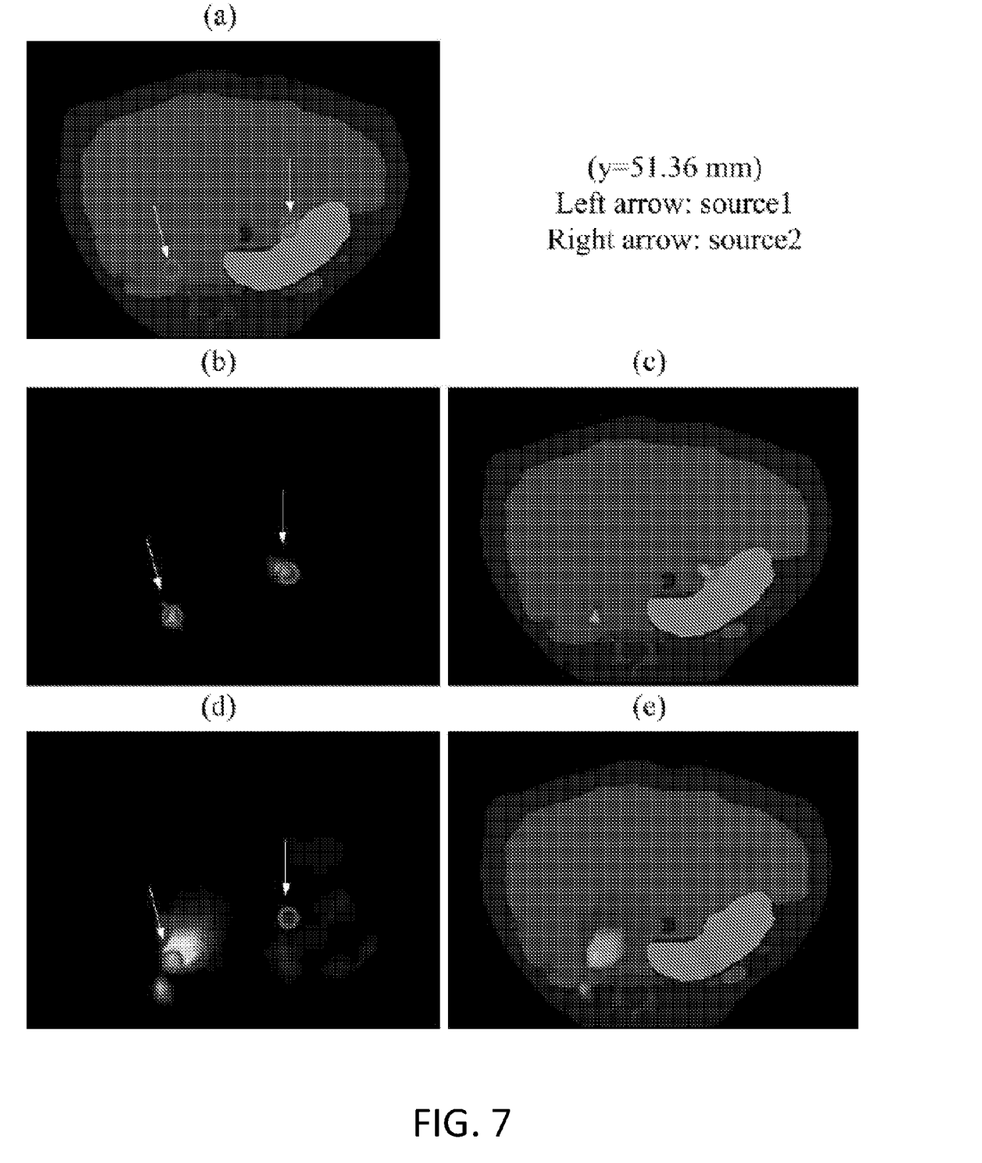
FIG. 7 shows reconstruction results of light sources in a liver (a) shows the coronal slice based on micro-CT data. (b) and (d) show the reconstruction results based on RIRM and L1-RMRM, respectively. (c) and (e) show the reconstruction results based on two algorithms on XCT. Positions of the real light sources are marked by circles.

The first group: in the first experimental group, two spherical light sources with the radius of 1.5 mm were respectively placed in the liver and lung, the central position of which were (14, 51, 16) mm and (21, 51, 16) mm, and the distance from the organism surface were 5.56 mm and 5.82 mm, respectively. The reconstruction was respectively performed using the algorithm proposed in this disclosure and L1 regularization method, and the reconstruction results were shown in FIG. 7. The bioluminescent source can be reconstructed accurately using both algorithms, as shown in FIG. 7.

Figure 8:
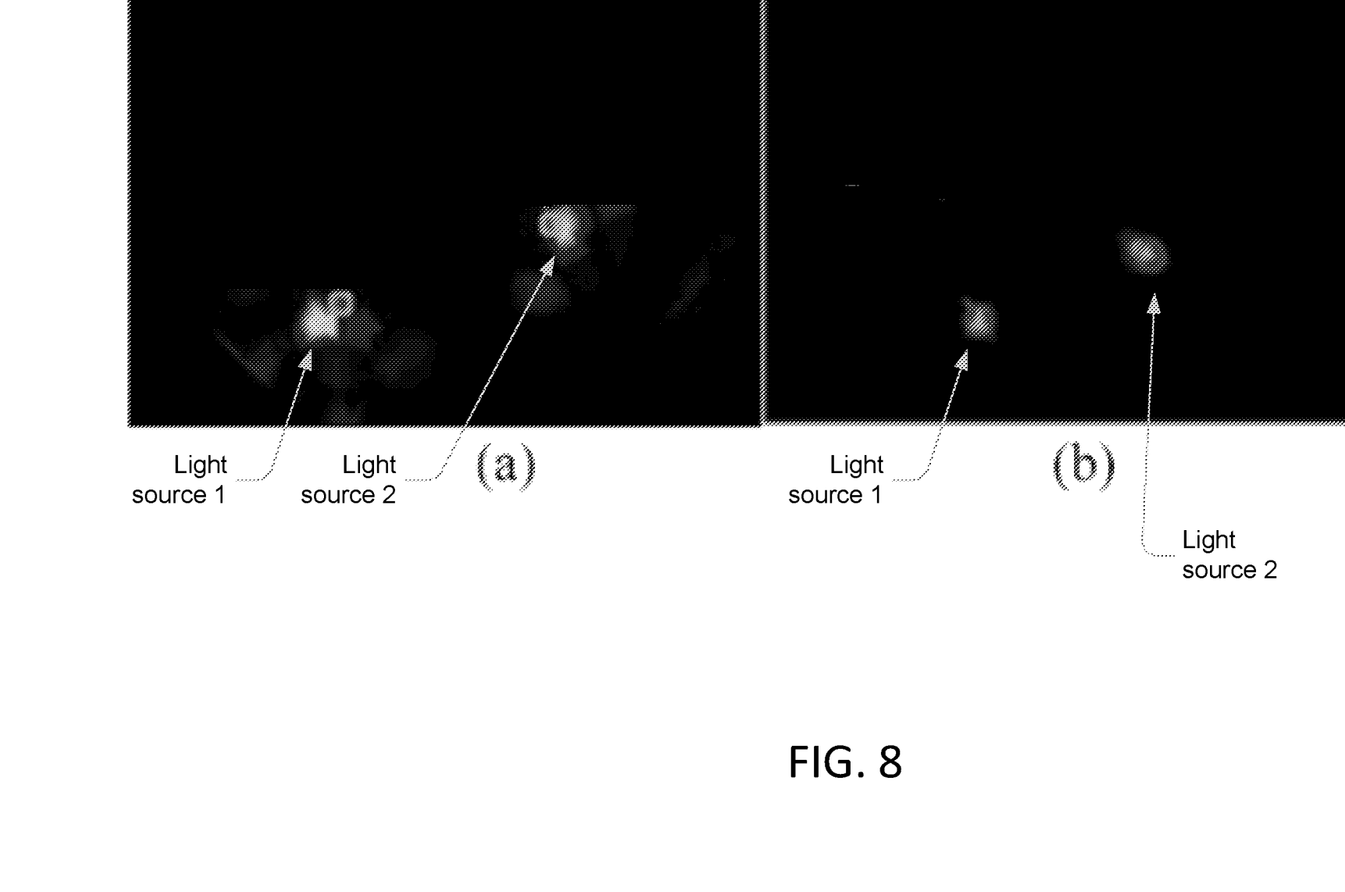
FIG. 8 shows reconstruction results of light sources (a) shows the reconstruction results based on Bayesian compressed sensing method, (b) shows the reconstruction results based on the proposed algorithm. The positions of the real light sources are marked by circles.

The second group: in the second experimental group, both of two light sources were placed in the liver, the light sources were reconstructed using the above two algorithms and reconstruction results were shown in FIG. 8. As shown in FIG. 8, only one light source was reconstructed based on L1 regularization method; whereas both of two bioluminescent sources can be reconstructed accurately using the algorithm proposed in the disclosure, which further verified the effectiveness of the proposed method.

The summarizing quantitative comparison of two group experiments of double light sources was performed, and the results were shown in table 3.

TABLE 3

The Summarizing Quantitative Comparisons between Two Algorithms Based on Double Light Source

| Biological Tissues Light Sources Located in | Reconstruction Algorithm | Position Error (mm) | | Reconstruction Time(s) |
|---|---|---|---|---|
| | | Light Source 1 | Light Source 2 | |
| Lung and Liver | IRIRM | 0.6772 | 0.3735 | 0.9828 |
| | L1-RMRM | 0.6772 | 0.3735 | 1770.6 |
| Liver | IRIRM | 1.0973 | 0.3330 | 0.4836 |
| | L1-RMRM | NaN | 0.3330 | 1767.7 |

In the disclosure, the simulation experiments were performed by setting a single light source in a lung and liver of the mouse-shape phantoms, and the algorithm proposed in the disclosure and reconstruction method based on L1 regularization were compared. Further, the experiments of double light sources were performed, the light sources were respectively reconstructed using the algorithm proposed in the disclosure and the reconstruction method based on L1 regularization, and the results were compared. Experimental results suggested the bioluminescent source can be reconstructed and located accurately using the proposed algorithm, and computational effectiveness can be greatly improved, which further testify the effectiveness of the proposed algorithm.

What is claimed is:

1. A method for bioluminescence tomography reconstruction using multitask Bayesian compressed sensing, the method comprising:

performing three-dimensional reconstruction of a bioluminescent source based on a high order approximation model associated with light propagation in a biological tissue, inner-correlation among multispectral measurements associated with a multitask learning method and incorporation of a reconstruction algorithm as prior information to reduce ill-posedness of BLT reconstruction by:

(Step one) defining problems and performing initialization by acquiring P wavelengths' boundary data at M measurement points, and setting gamma prior distribution $\alpha_0$ with a shape parameter a and scale parameter b, wherein $\alpha_0^{-1}$ is a variance of emission light measurements $\Phi(\tau_i)$ with Gaussian distribution, wherein each of two models is adopted to simulate the law of light propagation in the biological tissue, the two models include radiative transfer equation and diffusion equation, the radiative transfer equation is a mathematical model that describes the law of light propagation accurately, diffusion equation is low-order approximation of the radiative transfer equation, the application of the diffusion equation meets the conditions of biological tissues with strong scattering and low absorption, and the light source is not located on the boundaries of biological tissues, simplified spherical harmonics approximation ($SP_N$) equation is adopted thereof, the high order approximation model describes the light propagation in the biological tissue with strong scattering and low absorption and simulate the law of the light propagation in biological tissues to improve the precision of forward solution, given effect of spectrum, $SP_7$ model includes four equations at band $\tau_i$ and position r:

$$-\nabla \cdot \frac{1}{3\mu_{a1}(r,\tau_i)} \nabla \varphi_1(r,\tau_i) + \mu_a(r,\tau_i)\varphi_1(r,\tau_i) = \quad (1)$$

$$S(r,\tau_i) + \left(\frac{2}{3}\mu_a(r,\tau_i)\right)\varphi_2(r,\tau_i) -$$

$$\left(\frac{8}{15}\mu_a(r,\tau_i)\right)\varphi_3(r,\tau_i) + \left(\frac{16}{35}\mu_a(r,\tau_i)\right)\varphi_4(r,\tau_i),$$

$$-\nabla \cdot \frac{1}{7\mu_{a3}(r,\tau_i)} \nabla \varphi_2(r,\tau_i) + \left(\frac{4}{9}\mu_a(r,\tau_i) + \frac{5}{9}\mu_{a2}(r,\tau_i)\right)\varphi_2(r,\tau_i) = \quad (2)$$

$$-\frac{2}{3}S(r,\tau_i) + \left(\frac{2}{3}\mu_a(r,\tau_i)\right)\varphi_1(r,\tau_i) +$$

$$\left(\frac{16}{45}\mu_a(r,\tau_i) + \frac{4}{9}\mu_{a2}(r,\tau_i)\right)\varphi_3(r,\tau_i) -$$

$$\left(\frac{32}{105}\mu_a(r,\tau_i) + \frac{8}{21}\mu_{a2}(r,\tau_i)\right)\varphi_4(r,\tau_i),$$

-continued $$-\nabla \cdot \frac{1}{11\mu_{a5}(r,\tau_i)} \nabla \varphi_3(r,\tau_i) + \quad (3)$$

$$\left(\frac{64}{225}\mu_a(r,\tau_i) + \frac{16}{45}\mu_{a2}(r,\tau_i) + \frac{9}{25}\mu_{a4}(r,\tau_i)\right)\varphi_3(r,\tau_i) =$$

$$\frac{8}{15}S(r,\tau_i) - \left(\frac{8}{15}\mu_a(r,\tau_i)\right)\varphi_1(r,\tau_i) +$$

$$\left(\frac{16}{45}\mu_a(r,\tau_i) + \frac{4}{9}\mu_{a2}(r,\tau_i)\right)\varphi_2(r,\tau_i) +$$

$$\left(\frac{128}{525}\mu_a(r,\tau_i) + \frac{32}{105}\mu_{a2}(r,\tau_i) + \frac{54}{175}\mu_{a4}(r,\tau_i)\right)\varphi_4(r,\tau_i),$$

$$-\nabla \cdot \frac{1}{15\mu_{a7}(r,\tau_i)} \nabla \varphi_4(r,\tau_i) + \quad (4)$$

$$\left(\frac{256}{225}\mu_a(r,\tau_i) + \frac{64}{245}\mu_{a2}(r,\tau_i) + \frac{324}{1225}\mu_{a4}(r,\tau_i) + \frac{13}{49}\mu_{a6}(r,\tau_i)\right)$$

$$\varphi_4(r,\tau_i) = -\frac{16}{35}S(r,\tau_i) + \left(\frac{16}{35}\mu_a(r,\tau_i)\right)\varphi_1(r,\tau_i) -$$

$$\left(\frac{32}{105}\mu_a(r,\tau_i) + \frac{8}{21}\mu_{a2}(r,\tau_i)\right)\varphi_2(r,\tau_i) +$$

$$\left(\frac{128}{525}\mu_a(r,\tau_i) + \frac{32}{105}\mu_{a2}(r,\tau_i) + \frac{54}{175}\mu_{a4}(r,\tau_i)\right)\varphi_3(r,\tau_i),$$

wherein S represents light function, $\mu_a$ is a light absorption coefficient; $\mu_s$ is a light scattering coefficient; $\mu_{ai}=\mu_a+\mu_s(1-g^i)$, $g^i$ is anisotropic factor, $\varphi_i$ represents a linear combination of Legendre moments $\phi_i$ of radiosity and is represented as:

$$\begin{cases} \varphi_1 = \phi_0 + 2\phi_2 \\ \varphi_2 = 3\phi_2 + 4\phi_4 \\ \varphi_3 = 5\phi_4 + 6\phi_6 \\ \varphi_4 = 7\phi_6, \end{cases}$$

based on the $SP_7$ equation, setting $\phi_6=\phi_4=0$ and remain formula (1) and (2), and $SP_3$ equations are obtained:

$$-\nabla \cdot \frac{1}{3\mu_{a1}(r,\tau_i)} \nabla \varphi_1(r,\tau_i) + \quad (6)$$

$$\mu_a(r,\tau_i)\varphi_1(r,\tau_i) - \frac{2}{3}\mu_a(r,\tau_i)\varphi_2(r,\tau_i) = S(r,\tau_i)$$

$$-\left(\frac{2}{3}\mu_a(r,\tau_i)\right)\varphi_1(r,\tau_i) - \nabla \cdot \frac{1}{7\mu_{a3}(r,\tau_i)} \nabla \varphi_2(r,\tau_i) + \quad (7)$$

$$\left(\frac{4}{9}\mu_a(r,\tau_i) + \frac{5}{9}\mu_{a2}(r,\tau_i)\right)\varphi_2(r,\tau_i) = -\frac{2}{3}S(r,\tau_i),$$

based on the boundary conditions of $SP_7$, setting $\phi_6=\phi_4=0$, wherein the boundary conditions of $SP_3$ are obtained:

$$\left(\frac{1}{2} + A_1\right)\varphi_1(r,\tau_i) + \left(\frac{1+B_1}{3\mu_{a1}(r,\tau_i)}\right)\vec{n}(r,\tau_i) \cdot \nabla \varphi_1(r,\tau_i) = \quad (8)$$

$$\left(\frac{1}{8} + C_1\right)\varphi_2(r,\tau_i) + \left(\frac{D_1}{\mu_{a3}(r,\tau_i)}\right)\vec{n}(r,\tau_i) \cdot \nabla \varphi_2(r,\tau_i)$$

$$\left(\frac{7}{24} + A_2\right)\varphi_2(r,\tau_i) + \left(\frac{1+B_2}{7\mu_{a3}(r,\tau_i)}\right)\vec{n}(r,\tau_i) \cdot \nabla \varphi_2(r,\tau_i) = \quad (9)$$

$$\left(\frac{1}{8} + C_2\right)\varphi_1(r,\tau_i) + \left(\frac{D_2}{\mu_{a1}(r,\tau_i)}\right)\vec{n}(r,\tau_i) \cdot \nabla \varphi_1(r,\tau_i),$$

wherein $\vec{n}$ represents the outward unit normal vector which is perpendicular to the boundary, $A_i$, $B_i$ and $C_i$ are a series of constants, related to the angle distance of boundary reflectivity; the corresponding surface emission light $\Phi(r, \tau_i)$ is:

$$\Phi(r, \tau_i) = \left(\frac{1}{4} + J_0\right)\varphi_1(r, \tau_i) - \left(\frac{0.5 + J_1}{3\mu_{a1}\varphi_1(r, \tau_i)}\right)\vec{n} \cdot \nabla \varphi_1(r, \tau_i) - \left(\frac{1}{16} + \frac{2J_0 - J_2}{3}\right)\varphi_2(r, \tau_i) - \left(\frac{J_3}{7\mu_{a1}\varphi_2(r, \tau_i)}\right)\vec{n} \cdot \nabla \varphi_2(r, \tau_i),$$

wherein, $J_0, \ldots, J_3$ are a series of constants;

(Step two) constructing the linear relationship based on finite element method to discretize $SP_3$ diffusion equation, and constructing the linear model between boundary measurements and unknown light source for each wavelength, wherein, in the formula (6) and (7), $S(r, \tau_i)$ represents the distribution of bioluminescent light source and also the unknown quantity to be solved, incorporating two SP3 equations should be written in corresponding weak solution forms to solve the $SP_3$ equation and related boundary conditions using finite element method:

$$\int_\Omega \left(-\nabla \cdot \frac{1}{3\mu_{a1}(r, \tau_i)}\nabla \varphi_1(r, \tau_i) + \mu_a(r, \tau_i)\varphi_1(r, \tau_i) - \frac{2}{3}\mu_a(r, \tau_i)\varphi_2(r, \tau_i)\right)$$
$$\Psi(r, \tau_i)dr = \int_\Omega S(r, \tau_i)\Psi(r, \tau_i)dr,$$

$$\int_\Omega \left(-\left(\frac{2}{3}\mu_a(r, \tau_i)\right)\varphi_1(r, \tau_i) - \nabla \cdot \frac{1}{7\mu_{a3}(r, \tau_i)}\nabla \varphi_2(r, \tau_i) + \left(\frac{4}{9}\mu_a(r, \tau_i) + \frac{5}{9}\mu_{a2}(r, \tau_i)\right)\varphi_2(r, \tau_i)\right)$$
$$\Psi(r, \tau_i)dr = \int_\Omega \left(-\frac{2}{3}S(r, \tau_i)\right)\Psi(r, \tau_i)dr$$

wherein $\Psi(r, \tau_i)$ is test function,

Incorporating two boundary conditions for the formula (8) and (9) in corresponding weak solution forms:

$$\int_\Omega \left(\left(\frac{1}{2} + A_1\right)\varphi_1(r, \tau_i) + \left(\frac{1 + B_1}{3\mu_{a1}(r, \tau_i)}\right)\vec{n}(r, \tau_i) \cdot \nabla \varphi_1(r, \tau_i)\right)\Psi(r, \tau_i)dr =$$
$$\int_\Omega \left(\left(\frac{1}{8} + C_1\right)\varphi_2(r, \tau_i) + \left(\frac{D_1}{\mu_{a3}(r, \tau_i)}\right)\vec{n}(r, \tau_i) \cdot \nabla \varphi_2(r, \tau_i)\right)\Psi(r, \tau_i)dr,$$

$$\int_\Omega \left(\left(\frac{7}{24} + A_2\right)\varphi_2(r, \tau_i) + \left(\frac{1 + B_2}{7\mu_{a3}(r, \tau_i)}\right)\vec{n}(r, \tau_i) \cdot \nabla \varphi_2(r, \tau_i)\right)\Psi(r, \tau_i)dr =$$
$$\int_\Omega \left(\left(\frac{1}{8} + C_2\right)\varphi_2(r, \tau_i) + \left(\frac{D_2}{\mu_{a1}(r, \tau_i)}\right)\vec{n}(r, \tau_i) \cdot \nabla \varphi_1(r, \tau_i)\right)\Psi(r, \tau_i)dr,$$

incorporating the weak solution forms of the boundary conditions into that for the $SP_3$ equation using Green's formula;

$$\int_\Omega \left(\frac{1}{3\mu_{a1}}\nabla \varphi_1(r, \tau_i) + \mu_a\varphi_1(r, \tau_i)\psi(r, \tau_i) - \frac{2}{3}\mu_a\varphi_2(r, \tau_i)\psi(r, \tau_i)\right)dr -$$
$$\int_{\partial\Omega} \left(\frac{e_1}{3\mu_{a1}}\nabla \varphi_1(r, \tau_i) + \frac{e_2}{3\mu_{a1}}\varphi_2(r, \tau_i)\right)\psi(r, \tau_i)dr =$$
$$\int_\Omega S(r, \tau_i)\psi(r, \tau_i)dr,$$

$$\int_\Omega \left(\frac{1}{7\mu_{a3}(r, \tau_i)}\nabla \varphi_2(r, \tau_i) \cdot \nabla \psi(r, \tau_i) + \left(\frac{4}{9}\mu_a(r, \tau_i) + \frac{5}{9}\mu_{a2}(r, \tau_i)\right)\varphi_2(r, \tau_i)\psi(r, \tau_i) - \left(\frac{2}{3}\mu_a(r, \tau_i)\right)\varphi_1(r, \tau_i)\psi(r, \tau_i)\right)dr = \int_\Omega \left(-\frac{2}{3}S(r, \tau_i)\right)\psi(r, \tau_i)dr,$$

wherein $e_1$, $e_2$, $e_3$ and $e_4$ are respectively:

$$e_1 = \frac{1}{W}\left(\frac{D_1(1 + 8C_2)}{8\mu_{a3}} - \frac{(1 + B_2)(1 + 2A_1)}{14\mu_{a3}}\right),$$

$$e_2 = \frac{1}{W}\left(\frac{(1 + B_2)(1 + 8C_2)}{56\mu_{a3}} - \frac{D_1(7 + 24A_2)}{24\mu_{a3}}\right),$$

$$e_3 = \frac{1}{W}\left(\frac{(1 + B_1)(1 + 8C_2)}{24\mu_{a1}} - \frac{D_2(7 + 2A_1)}{2\mu_{a1}}\right),$$

$$e_4 = \frac{1}{W}\left(\frac{D_2(1 + 8C_1)}{8\mu_{a1}} - \frac{(1 + B_1)(7 + 24A_2)}{72\mu_{a1}}\right),$$

wherein in the above formulas, the form for W is as follow:

$$W = \frac{(1 + B_1)(1 + B_2)}{21\mu_{a1}\mu_{a3}} - \frac{D_1D_2}{\mu_{a1}\mu_{a3}},$$

wherein, for mesh generation, the distribution of light source $S(r, \tau_i)$ is written as $S(\tau_i)$ related to the spectral band, when the corresponding basis function is selected, the whole stiffness matrix $M_{ij}$ is assembled, discretizing the $SP_3$ equation into the matrix equation as follow:

$$\begin{bmatrix} M_{11} & M_{12} \\ M_{21} & M_{22} \end{bmatrix}\begin{bmatrix} \varphi_1 \\ \varphi_2 \end{bmatrix} = \begin{bmatrix} B & 0 \\ 0 & B \end{bmatrix}\begin{bmatrix} S(\tau_i) \\ -\frac{2}{3}S(\tau_i) \end{bmatrix},$$

wherein B is the matrix of size N×N, $\phi_1$ and $\phi_1$ are two partitioned submatrices and are represented as:

$\phi_1 = \frac{1}{3}B[3M_{12}^{-1} + 2M_{22}^{-1}IM_{11}^{-1}M_{12} + 2M_{21}^{-1}M_{22}]^{-1}S(\tau_i),$ $\phi_2 = \frac{1}{3}B[3M_{11}^{-1} + 2M_{21}^{-1}IM_{11}^{-1}M_{12} + 2M_{21}^{-1}M_{22}]^{-1}S(\tau_i),$ wherein the linear relationship between the surface emission light $\Phi(\tau_i)$ and the distribution of unknown bioluminescent light source $S(\tau_i)$ are constructed, in the experiment, only the optical signals on the surface of organisms are collected such that only the node values on the boundary of $\Phi(\tau_i)$ is remained and the rows which do not contain the nodes on the boundary of matrix are removed, and the equation is obtained as follow:

$\Phi(\tau_i) = \beta_1\phi_1 + \beta_2\phi_2 = \frac{1}{3}B(\beta_1[3M_{12}^{-1} + 2M_{22}^{-1}IM_{11}^{-1}M_{12} + 2M_{21}^{-1}M_{22}]^{-1} + \beta_2[3M_{11}^{-1} + 2M_{21}^{-1}IM_{11}^{-1}M_{12} + 2M_{21}^{-1}M_{22}]^{-1}S(\tau_i) = A(\tau_i)S(\tau_i),$ wherein the above equation constructs the relationship between the distribution of unknown bioluminescent light source and the boundary emission light, which is:

$\Phi(\tau_i) = A(\tau_i)S(\tau_i)$ wherein, in multispectral conditions, the energy ratio $\omega(\tau_i)$ of spectral bands is measured by spectrum analysis in advance, setting S to represent the total energy of all spectral bands of light sources, which is $S=\Sigma_{i=1}^{P} \omega(\tau_i)S(\tau_i)$, and p to represent the number of spectral bands, wherein all spectral bands of light sources and boundary measurements are incorporated, the relationship between the distribution of unknown bioluminescent light source and the boundary emission light in multispectral conditions is formulated as follow:

$A_{mul}S=\Phi_{mul}$

Now, $$A_{mul} = \begin{bmatrix} \omega(\tau_1)A(\tau_1) \\ \omega(\tau_2)A(\tau_2) \\ \vdots \\ \omega(\tau_P)A(\tau_P) \end{bmatrix}, \Phi_{mul} = \begin{bmatrix} \Phi(\tau_1) \\ \Phi(\tau_2) \\ \vdots \\ \Phi(\tau_P) \end{bmatrix};$$

(Step three) estimating the shared prior based on empirical Bayesian maximum likelihood function, infer parameter $\alpha$ which represents the correlation among multi-wavelength;

wherein, the emission light measurement $\Phi(\tau_i)$ contains noise, if the noise obeys Gaussian random distribution with mean zero and variance $\alpha_0^{-1}$, the maximum likelihood function of $\Phi(\tau_i)$ related to the distribution of bioluminescent light source $S(\tau_i)$ and $\alpha_0$ is represented as:

$$p(\Phi(\tau_i)|S(\tau_i),\alpha_0) = \left(\frac{\alpha_0}{2\pi}\right)^{\frac{M}{2}} \exp\left\{-\frac{\alpha_0}{2}\|\Phi(\tau_i)-A(\tau_i)S(\tau_i)\|_2^2\right\},$$

introducing a multitask idea is introduced to describe the correlation among spectral bands, wherein the whole light source is regarded as a whole task T, $S(\tau_i)$ is the ith task model of T, and $S_j(\tau_i)$ represents the jth element of $S(\tau_i)$, and if $S(\tau_i)$ obeys the Gaussian prior distribution with mean zero and the parameter $\alpha_0$ obeys Gamma prior distribution, then:

$p(S(\tau_i)|\alpha,\alpha_0) = \Pi_{j=1}^{N} N(S_j(\tau_i)|0,\alpha_0^{-1}\alpha_j^{-1})$, $p(\alpha_0|a,b) = Ga(\alpha_0|a,b)$, wherein $\alpha=(\alpha_1, \ldots \alpha_j, \ldots \alpha_N)^T$ NY is hyper-parameter, representing prior information, the values of $\alpha_j$ are identical in all spectral bands, i.e. $\alpha$ representing the correlation among various spectral bands, an empirical Bayesian method that estimates the hyper-parameter $\alpha$ is used by maximizing a marginal likelihood function, then:

$$L = \sum_{i=1}^{P} \log p(\Phi(\tau_i)|\alpha) =$$

$$\sum_{i=1}^{P} \log\left(\int P(\Phi(\tau_i)|S(\tau_i),\alpha_0)P(S(\tau_i)|\alpha,\alpha_0|a,b)\right)dS_{\tau_i}d\alpha_0 =$$

$$-\frac{1}{2}\sum_{i=1}^{P}\left[(n_i+2a)\log(\Phi(\tau_i)^T B_i^{-1}\Phi(\tau_i)+b) + \frac{\log|B_i|}{2}\right] + const$$

wherein $B_i = I + A(\tau_i)\Lambda^{-1} A(\tau_i)^T$, $\Lambda^{-1} = \text{diag}(\alpha_1, \alpha_1, \ldots, \alpha_N)$; and (Step four) reconstructing an unknown light source based on the estimated $\hat{\alpha}$ of the known hyper-parameter and boundary measurements $\Phi_{mul}$, wherein the bioluminescent light source is reconstructed using maximum likelihood function, after obtaining the estimated $\hat{\alpha}$, incorporating all spectral bands of light sources and boundary measurements, wherein the maximum likelihood function of the unknown light source S is represented as:

$$P(S|\Phi_{mul},\hat{\alpha}) = \int P(S|\Phi_{mul},\hat{\alpha},\alpha_0)P(\alpha_0|a,b)d\alpha_0 =$$

$$\frac{\Gamma\left(a+\frac{N}{2}\right)\left[1+\frac{1}{2b}(S-\mu_{mul})^T\sum_{mul}^{-1}(S-\mu_{mul})\right]^{-\left(a+\frac{N}{2}\right)}}{\Gamma(a)(2\pi b)^{N/2}|\sum_{mul}|^{1/2}},$$

wherein, $\mu_{mul} = \Sigma_{mul}A_{mul}^T\Phi^{mul}$ $\Sigma mul = (A_{mul}^T A_{mul}+\Xi)^{-1}$, and wherein, in the formula, $\Xi = \text{diag}(\hat{\alpha}_1, \hat{\alpha}_1, \ldots, \hat{\alpha}_N)$.

* * * * *